US00PP18602P3

(12) United States Plant Patent

Jeske et al.

(10) Patent No.: US PP18,602 P3

(45) Date of Patent: Mar. 18, 2008

(54) HOP PLANT NAMED 'BRAVO'

(50) Latin Name: *Humulus lupulus L.*
Varietal Denomination: BRAVO

(75) Inventors: Roger D. Jeske, Yakima, WA (US); Joe Brulotte, Yakima, WA (US)

(73) Assignee: S.S. Steiner, Inc., New York, NY (US)

( * ) Notice: Subject to any disclaimer, the term of this patent is extended or adjusted under 35 U.S.C. 154(b) by 54 days.

(21) Appl. No.: 11/344,245

(22) Filed: Jan. 31, 2006

(65) Prior Publication Data

US 2006/0218683 P1 Sep. 28, 2006

(51) Int. Cl.
*A01H 5/00* (2006.01)

(52) U.S. Cl. ..... Plt./236

(58) Field of Classification Search ..... Plt./236
See application file for complete search history.

*Primary Examiner*—Kent Bell
*Assistant Examiner*—S. B. McCormick-Ewoldt
(74) *Attorney, Agent, or Firm*—Hayes Soloway P.C.

(57) ABSTRACT

A new and distinct variety of hop, *Humulus lupulus* L., named "01046" is characterized by its exceptional cone yield, high percentage of alpha acids, and resistance to hop powdery mildew strains found in Washington. The new variety was cultivated as a result of a cross in 2000 at Golden Gate Roza Hop Ranches in Prosser, Wash., United States and has been asexually reproduced in Prosser, Wash., United States.

2 Drawing Sheets

BACKGROUND OF INVENTION

The flowers (cones) of the female hop plant, *Humulus lupulus* L, are used in the making of beverages, especially beer, as a flavoring and processing component. Hops contribute towards the bitterness and aroma in beer as well as foam quality and flavor and taste stability.

Hop plants, hops cones, male hop flowers, hop plant parts, hop tissue cultures and hop extracts also have bioactive properties; including anti-microbial, anti-cancer, anti-osteoporosis, anti-oxidative, anti-inflammatory, antibiotic, soporific, anti-androgenic, and pro-estrogenic activities, among others; which may be used in herbal remedies, in antimicrobial preparations for food, fodder, food fermentation, food process, animal husbandry; or in non-food uses, such as composting, biofuel processing, fermentation process, water treatment, animal bedding and phytoremediation; and uses in cosmetics, in nutraceutical and in pharmaceutical applications and in research thereof. Examples activities and non-berverage uses are included herein by references: J Hazard Mater. Apr. 26;91(1–3):95–112; Mol Cancer Ther. Sep;1(11):959–69; Phytochemistry. May;65(10):1317–30; U.S. Pat. No. 6,423,317 (2002); U.S. Pat. No. 6,623,775 (2003).

Agricultural end-product users, growers, handlers and processors of hops, of hop plants, of hop tissues and of hop products use hops and are affected by the agronomic, developmental, morphological, chemical and physical properties that vary among unique and distinct asexually reproduced varieties. This invention relates to an asexually produced hop variety, named "BRAVO", invented in a planned and symmetrically executed breeding program.

SUMMARY OF INVENTION

This invention relates to a new genetically, chemically, and morphologically distinct variety of hop selected from among the multitude of hop plants resulting from a controlled cross-pollination during the summer of 2000. The cross-pollination was between a proprietary non-patented female hop plant referred to as "Zeus" with a proprietary non-patented male hop plant (98004×USDA 19058m)m. The parents of "98004" (non-patented) are female hop plant "Nugget" (commercially available and non-patented) and a non-patented male progeny of open pollinated "Nugget".

The cross-pollination resulting in "BRAVO" was performed in 2000 by Roger Jeske, one of the named inventors in a field in Prosser, Wash. During 2001 seeds collected from the cross-pollination were germinated and screened for powdery mildew resistance in a greenhouse in Prosser, Wash. These seedlings were planted in a field nursery and further screened for gender, vigor, cone type, and disease resistance with the best genotypes being advanced to a single hill hop nursery during the spring of 2002. Mr. Jeske discovered the "BRAVO" variety during the summer of 2002 among the numerous hop genotypes growing in a single hill hop nursery in Prosser, Wash. These hop genotypes growing in the single hill hop nursery were grown in a 3.5'×14' spacing on twine attached to an 18' trellis system.

Chemical analysis and field observations in 2002 demonstrated unusually high percentage of alpha-acids, lack of powdery mildew in the leaves and cones, and an exceptional cone set. Cones were compact and easy to pick with no shatter. Vigor was excellent and yield potential appeared to be exceptional, although yield data was not taken in 2002.

In 2003, "BRAVO" was asexually propagated in greenhouses at Prosser, Wash. Rhizomes from the original single hill plant of "BRAVO" were dug, divided and planted into multiple greenhouse grown containers. Softwood cuttings were periodically taken from these original containers until approximately 4,000 softwood-cutting plants were made. These plants constituted the first asexual reproduction of the "BRAVO" variety and are the second generation. They were grown at two geographical locations with no powdery mildew observed. These two small scale trials consisted of a multi-hill planting (7 plants) located in fields in Prosser, Wash. and a multi-hill planting (7 plants) in fields located in Sunnyside, Wash. These trials were subjected to standard agronomic, cultural and management practices for the purposes of determining harvest ability, yield, chemical characteristics, and process ability. Also, established in 2003 was a large-scale trial of second-generation plants north of Prosser, Wash. This consisted of planting two acres in a 3.5'×14' configuration (1778 hills), with two softwood cuttings of "BRAVO" planted per hill.

During 2003, 2004, and 2005 second-generation plants in the two small-scale trials and one large-scale trial at in fields in Prosser, Wash. were sampled for chemical analysis and harvested for yield evaluations. Results from the test plots provided additional information supporting the disease resistance, yield potential, and alpha-acids projections made from the original "BRAVO" plant (first generation) selected in 2002. This confirmed the exceptionally high yield and high alpha-acids percentages of the new variety. The 2003 harvest of greenhouse potted plant baby "BRAVO" yielded 2200 lbs./acre from the two-acre test plot of second-generation plants grown north of Prosser, Wash. The 2004–2005 commercially harvested two-acre test plot of second-generation plants produced an average of 3200 lbs/acre. Commercially harvested hop cones were kiln dried to approximately 10% moisture, then were pressed into 200 lb. bales. Bale samples from the 2003–2005 second generation "BRAVO" hops grown in field locations in Prosser, Wash. showed an average alpha-acids level of 17.5% and beta-acids level of 3.5% (American Society of Brewing Chemists spectrophotometric method). The percentage of alpha acids is nearly identical to the commercial variety "Zeus" non-patented, (mother of "BRAVO"). Storage stability of second generation "BRAVO" had an average loss of alpha-acids of the harvested hop cones stored at room temperature (22° C.) for six months of 33%. "Zeus", the mother of "BRAVO", by comparison had an average loss of alpha-acids of 48% in identical storage stability trials.

In 2005, the second asexual reproduction of the "BRAVO" variety took place. The second-generation rootstock from the two acres was dug, divided and planted into a larger acreage test plot near Sunnyside, Wash. These third generation plants were grown located in a field near Sunnyside, Wash., utilizing standard agricultural practices that are common for hop production, except no powdery mildew fungicides application was made. Third generation plants were sampled for chemical analysis and harvested for yield evaluations. Results from this third generation large-scale test plot provided additional information supporting the powdery mildew resistance and high alpha-acids percentages. The 2005 yield from these baby "BRAVO" plants was very good as compared to the baby yield of other commercial varieties.

Based on agronomic and chemical evaluations over a number of growing seasons both secondary and tertiary clones (second and third generations) of "BRAVO" exhibited genetic stability with respect to its novel characteristics of complete powdery mildew resistance, very high yield (>3000 lb./ac), and high alpha-acids percentages. This is in contrast to the mother, "Zeus", which is very susceptible to powdery mildew.

All observations, evaluations and testing of the "BRAVO" variety's agronomic, morphological, physical, and chemical properties were carried out by or directed by the inventors.

The variety "BRAVO" is very late maturing and is usually not ready to pick until the 20th to the 30th of September. The compact and ovoid shape cones of this variety are mid sized and very plentiful resulting in easy mechanical picking and cleaning much like "Nugget" (non-patented). The cones detach easily from stems, and the cones do not shatter during commercial harvesting and drying.

In order to demonstrate genetic and phenotypic distinctiveness to closely related varieties, "BRAVO" is compared to its mother and to other agronomically important varieties. "Zeus" (non-patented) is the parent of "BRAVO" and therefore similarities would be expected. The primary differences between the new "BRAVO" variety and "Zeus" is the complete resistance of "BRAVO" to the powdery mildew strains found in the Yakima Valley and improved storage stability of alpha acids as compared to "Zeus". Also, "BRAVO" mostly exhibits main bine leaves with three lobes as opposed to Zeus main bine leaves that are mostly five lobed. Similarities include similar cone shape and weight of 220–280 mg. at maturity, mature main bine of green coloration with violet stripes, and both varieties having excellent yields (>3000 lbs./ac). Chemical similarities show that both have alpha-acid levels of 16–18% and a humulene/caryophyllene ratio of 1.7

The detailed botanical description and drawings herein below allow distinction of the variety from related varieties. For illustration, comparisons of select distinguishing traits to further selected commercial varieties are set forth in Table 1.

TABLE 1

| | "BRAVO" | "Galena" | "Nugget" | "Zeus" |
|---|---|---|---|---|
| Alpha acids % w/w | 14-17 | 10-13.5 | 11-14 | 12-16.5 |
| Beta acids % w/w | 3.0-5.0 | 7.0-9.0 | 4.0-6.0 | 4.0-6.0 |
| CoH % w/w of alpha acids | 29-34 | 35-40 | 24-30 | 27-35 |
| Total Oil ml/100 g | 1.6-2.4 | 0.9-1.2 | 1.5-3.0 | 1.0-2.0 |
| Humulene % | 18-20 | 10-15 | 12-22 | 10-25 |
| Caryophyllene % | 10-12 | 3.0-5.0 | 7-10 | 5.0-15 |
| Powdery Mildew Disease | Resistant | Susceptible | Resistant | Susceptible |
| Cone Yield lbs/acre | 2800-3200 | 1600-2220 | 1700-2200 | 2400-3000 |

BRIEF DESCRIPTION OF THE DRAWINGS

The accompanying photographs illustrate the cones, leaves and growth habit of the new "BRAVO" variety.

GENERAL BOTANICAL DESCRIPTION OF THE VARIETY

Figure 1:
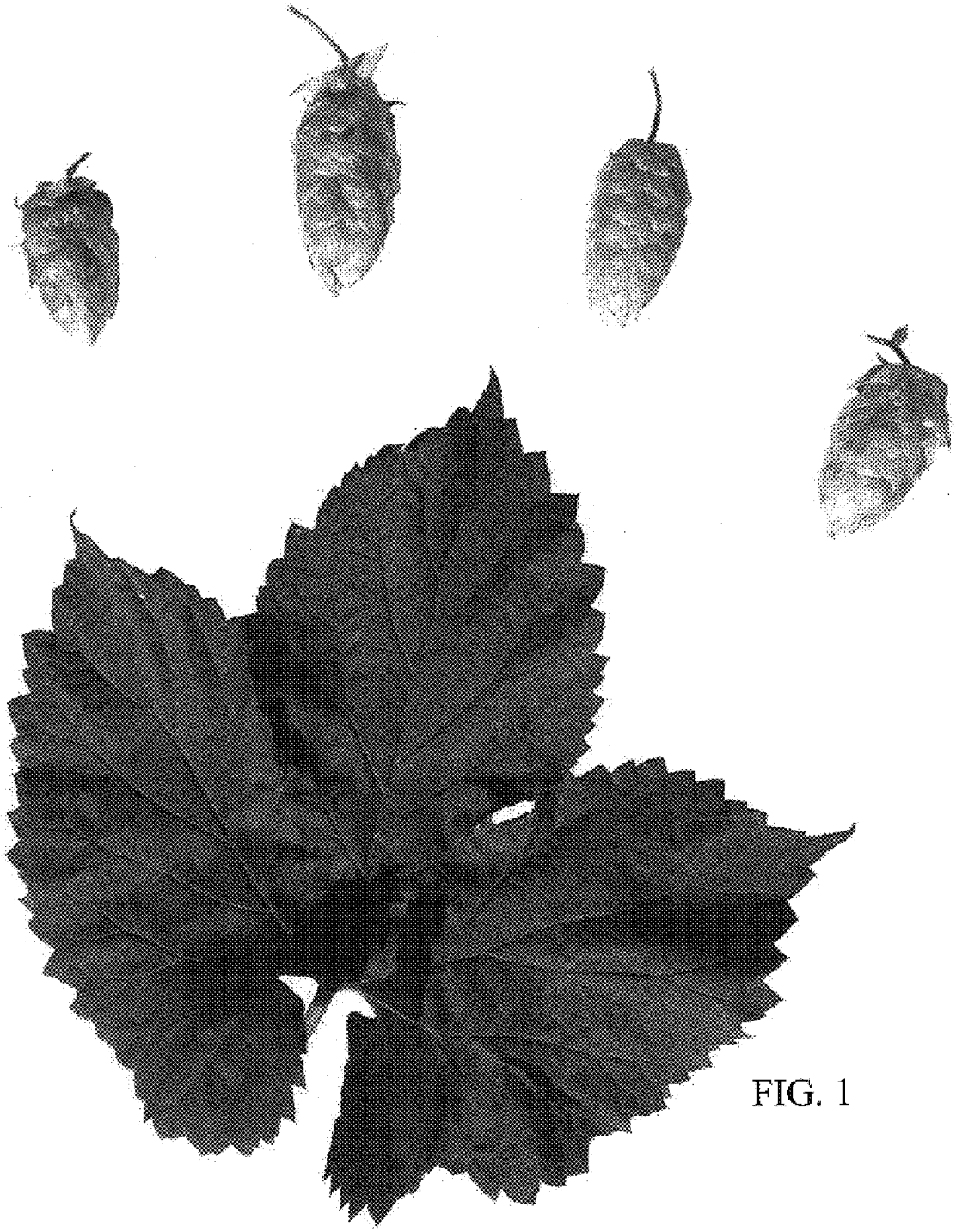
FIG. 1 depicts a close up of whole cones and mature main vine leaf.
Figure 2:
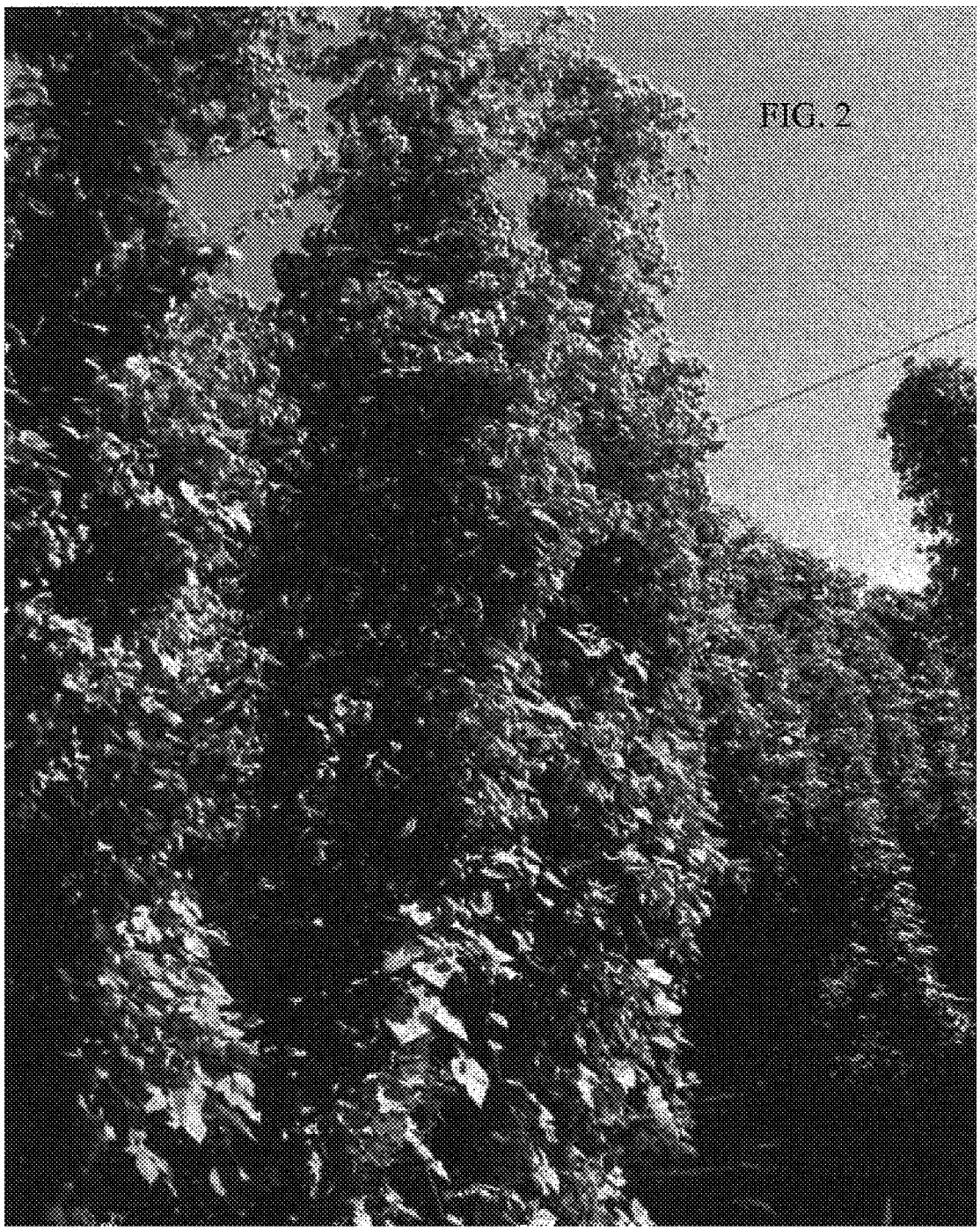
FIG. 2 depicts the appearance of the plants and cones as they are growing in the field on a high trellis (18') approaching harvest time.

This description provides information on agronomic, morphological, chemical and processing characteristics of the new variety that are used in distinction and identification of a new hop variety and its parts and products by practitioners of the industries that use hops as described herein above.

General information on the botanical characteristics and cultural aspects of hop plants as they relate to agronomics, breeding and food use are particularly well discussed in the prior art, especially, U.S. Plant Pat. Nos. 10,956 and 13,132 and the literature; "Steiner's Guide to American Hops Book III", 1986; "Hops" Published by Chapman and Hall, 1991. Detailed botanical information below of the present variety is directly comparable to the prior art, as contained by reference herein.

DETAILED BOTANICAL DESCRIPTION OF THE VARIETY

Following is a detailed description of the botanical and analytical chemical characteristics of the new variety. The information for this botanical description was either collected or verified during the growing seasons of 2002 through 2005 in the growing areas north of Prosser, Wash. and south of Sunnyside, Wash. Botanical characteristics, and to a lesser degree the analytical characteristics are somewhat dependent on cultural practices and climatic conditions and can vary with location or year.

1. Parentage: A hop plant originating from a controlled cross-pollination between proprietary non-patented female hop plant referred to as "Zeus" with a proprietary non-patented male hop plant (98004×USDA 19058m)m.
2. Locality where grown and observed: North of Prosser, Wash. and south of Sunnyside, Wash.
3. Agronomic factors: Dates of first and last harvest are approximately September 20 and September 30. Shoots of "BRAVO" emerge from winter dormancy about the same time as the commercial variety "Zeus" (non-patented). Emergence is typically by March 15$^{th}$ and the initial stem growth is fairly rapid like "Zeus" or "Nugget" (non-patented). "BRAVO" shows good vigor and a moderate growth rate. After spring pruning, growth continues to be average when compared to other commercial varieties. The main vine stems are green with violet shading (between RHS 146C and N77B). "BRAVO'S" main vine stems are mostly round to slightly hexagonal in cross section shape with 6 pronounced violet (RHS N77B) stripes, much like "Zeus", non-patented. Inflorescence of "BRAVO" begins to appear in the middle of July and mature during the forth week of September. Cone shape is fairly uniform in the "BRAVO" variety. The hop cones of "BRAVO" are well adapted to mechanical harvest because of their compactness and ovoid shape. The cones are similar to the variety "Nugget" (non-patented) and roll nicely on dribble belts, making cleaning easier. The cones do not shatter during harvest. In the following description color code designations are by reference to the R.H.S. Colour Chart, 4$^{th}$ Edition, provied by The Royal Horticultural Society of Great Britain.
4. Plant characteristics:
   *Plant.*—Vigorous, climbing vine.
   *Plant shape.*—Columnar. Bine color green with violet shading (between RHS 146C and N77B).
   *Bine stripe.*—Pink violet (RHS N77B).
   *Bine inter-node length (at 6' high).*—22 cm.
   *Bine diameter (at 6' high).*—1 cm.
   *Bine length.*—20–22'.
   *Petiole length.*—6–7 cm. Petiole color green with violet shading on upper surface (between RHS 144A and N77B).
   *Petiole shape.*—Slightly channeled (flat upper surface).
   *Leaf arrangement.*—Opposite.
   *Leaf shape.*—Cordate. Leaf color — upper surface — dark green — (RHS 137B). Leaf color — lower surface — green — (RHS 137C).
   *Mature leaf width.*—14–16 cm.
   *Mature leaf length.*—13–15 cm.
   *Number of main bine leaf lobes.*—Three.
   *Venation pattern.*—Toothed.
   *Vein color.*—Green (RHS 144A).
   *Leaf margin.*—Moderately serrate to dentate.
   *Lateral length (at 6' high).*—0.8–1.3 m.
   *Internode length of lateral (at 6' high).*—10–13 cm.
   *Stipule position.*—Outward-up, forked.
   *Stipule color.*—Green (RHS 146C).
5. Reproductive organs, cones, cone parts, seeds:
   *Bract color.*—(RHS 145A).
   *Bract tips shape.*—Acute to cuspidate.
   *Bract tip position.*—Mostly appressed.
   *Bracteole diameter.*—1.2 cm.
   *Bracteole shape.*—Lanceolate. Bracteole color — (RHS 145C).
   *Compactness.*—Tight to semi-dense.
   *Shape.*—Ovoid.
   *Cone length.*—3–4 cm.
   *Cone tip shape.*—Bluntly pointed.
   *Cone weight.*—220–280 mg.
   *Strig.*—Compact.
   *Lupulin glands.*—The cone of the present variety contains numerous lupulin glands.
   *Yield per acre.*—3000–3470 pounds on average. However, this yield is contingent upon temperature, soil conditions and cultural practices, and is therefore not distinctive of the present variety.
   *Seeds.*—Highly variable in color and size depending on male parent.
   *Date of maturity.*—Considered to be very late (September 20–30) as compared to other common hop varieties grown in central Washington.
6. Analytical data of cones:
   % *Alpha-acids (bale).*—14.0–17.0% (ASBC Spectrophotometric method).
   % *Beta-acids (bale).*—3.0–4.0% (ASBC Spectrophotometric method).
   *Alpha/beta ratio.*—4.5–5.5.
   *Cohumulone (% of alpha-acids).*—29–34%.
   *Storage characteristics.*—30–35% transformation of alpha acids after 6 months at 22° C.
   *Total oils (mls/100 g).*—1.6–2.4.
   *Humulene (% of total oils).*—18–20%.
   *Caryophyllene (% of total oils).*—10–12%.
   *Humulene/caryophyllene ratio.*—1.7.
   *Farnesene (% of total oils).*—0.5%.
   *Myrcene (% of total oils).*—25–50%.
7. Disease resistance: The variety "BRAVO" is resistant to the strains of powdery mildew fungus found in the Yakima Valley as of 2005, but since not all strains are present no future powdery mildew resistance can be assured. "BRAVO" appears to be tolerant to strains of *Verticillium* wilt and the virus diseases found in the USA growing areas. Susceptibility to hop downy mildew fungus is moderate and preventative measures are recommended. Tolerance to the major soil borne pests and diseases that affect hops is not known at this time.
8. Regional adaptation: The "BRAVO" variety is well adapted to the drier growing regions of Washington State, specifically the Yakima Valley. "BRAVO" has not been tested in other growing locations, but hop growing regions like the Willamette Valley of Oregon may not be suitable due to high humidity and the susceptibility of this variety to downy mildew infections.

9. Ploidy: Hop variety "BRAVO" is diploid. The mother is diploid and the father is diploid.
10. Life expectancy: Indefinite similar to other hop varieties.
11. Use: Flavoring and conditioning of beverages and foods and use as a vegetable. Constituent of herbal remedies, nutraceuticals, pharmaceuticals, drugs, ointments, antiseptic washes and cosmetics for humans and animals. Constituent of fodder, bedding, compost, agricultural treatments, phytoremediation treatments, water and soil treatments, conditioning of fermentation and other industrial processes. Used in breeding novel hop varieties.
12. Propagation status: "BRAVO" rootstock and plant propagation material exists. Asexual plant propagation has been demonstrated.
13. Reproductive status: "BRAVO" is fertile and produces seeds upon pollination with male hop plants.

DISTINGUISHING CHARACTERISTICS

This new hop variety "BRAVO" can be distinguished from all other USA commercial varieties by its resistance to powdery mildew in combination with a high percentage of alpha-acids, excellent yield, and late harvestability while maintaining excellent cone quality, allowing harvest until late September to early October.

We claim:

1. A new and distinct hop plant, named "BRAVO" as herein described and illustrated.

* * * * *